United States Patent [19]

Tokoyama

[11] Patent Number: 5,239,358
[45] Date of Patent: Aug. 24, 1993

[54] POWDER MATERIAL INSPECTION APPARATUS

[75] Inventor: Katsumi Tokoyama, Osaka, Japan
[73] Assignee: Hajime Industries, Tokyo, Japan
[21] Appl. No.: 653,669
[22] Filed: Feb. 8, 1991
[51] Int. Cl.⁵ .............................................. G01N 1/20
[52] U.S. Cl. ...................................... 356/244; 209/581
[58] Field of Search .................. 356/244, 36; 209/581, 209/643, 919, 939; 250/576

[56] References Cited

U.S. PATENT DOCUMENTS

| | | | |
|---|---|---|---|
| 2,645,343 | 7/1953 | Nemir | 209/581 |
| 2,726,762 | 12/1955 | Aubry | 209/581 |
| 3,943,771 | 3/1976 | Handa et al. | 356/244 |
| 4,351,437 | 9/1982 | Long | 209/939 |
| 4,830,194 | 5/1989 | Kajiura et al. | 209/643 |
| 4,976,540 | 12/1990 | Kitamura et al. | 356/237 |

FOREIGN PATENT DOCUMENTS 8701807 2/1989 Netherlands ..................... 209/643

Primary Examiner—Richard A. Rosenberger
Attorney, Agent, or Firm—Bauer & Schaffer

[57] ABSTRACT

Apparatus is provided for inspecting powder material and for removing the foreign matter therefrom. A rotary table is provided to receive powder material to be inspected on its surface. A feeder supplies the powder material onto the surface of the table aligned in a single layer and a photosensing system detects the foreign matter. The foreign matter is removed by a suction device. Thereafter, the remaining power material is removed by a second suction device.

9 Claims, 6 Drawing Sheets

POWDER MATERIAL INSPECTION APPARATUS

BACKGROUND OF THE INVENTION

1. Field of the Invention

The present invention relates generally to inspection apparatuses and is directed more particularly to an inspection apparatus that automatically conducts inspection of at least foreign material contained in an object to be inspected such as powder material or pharmaceutical products, plastic material, pulverized material or the like and removes such foreign material therefrom.

2. Description of the Prior Art

The assignee of the present application has readily developed an inspection apparatus that automatically conducts more than one item of inspection on powder granule materials of such products as pharmaceutical material, plastic material or the like, which has readily been submitted as a Japanese Utility Model Registration Application No. 63-67309.

However, according to this inspection apparatus, since the detection of foreign material within the powder material is carried out by a television camera that is installed above the rotary table on which the powder material is located, the foreign materials that can only be visualized from the underside of the rotary table are overlooked so that the foreign material inspection would be incomplete.

OBJECTS AND SUMMARY OF THE INSPECTION

Therefore, it is an object of the present invention to propose an inspection apparatus that enables the detection and removal of foreign material within the powder material with high reliability.

According to an aspect of the present invention, there is provided a powder material inspection apparatus for conducting automatic a foreign material inspection on powder material and for removing such foreign material detected, which comprises a rotary table that rotates and conveys thereon the powder material to be inspected, a feeder that supplies the powder material on the surface of the rotary table in a lined up single layer, photosensing system which picks up the powder material on the surface of the rotary table from the front side as well as the back side to detect the foreign material contained the powder material, a foreign material remover that removes the foreign material from the surface of the powder rotary table, and a power material remover which removes the powder material from the surface of the rotary table after the foreign material removal.

The additional, and other objects, features and advantages of the present invention will become apparent from the following description taken in conjunction with the accompanying drawings through which the same reference numerals designate the same or similar elements or parts.

DESCRIPTION OF THE PREFERRED EMBODIMENTS

Figure 1:
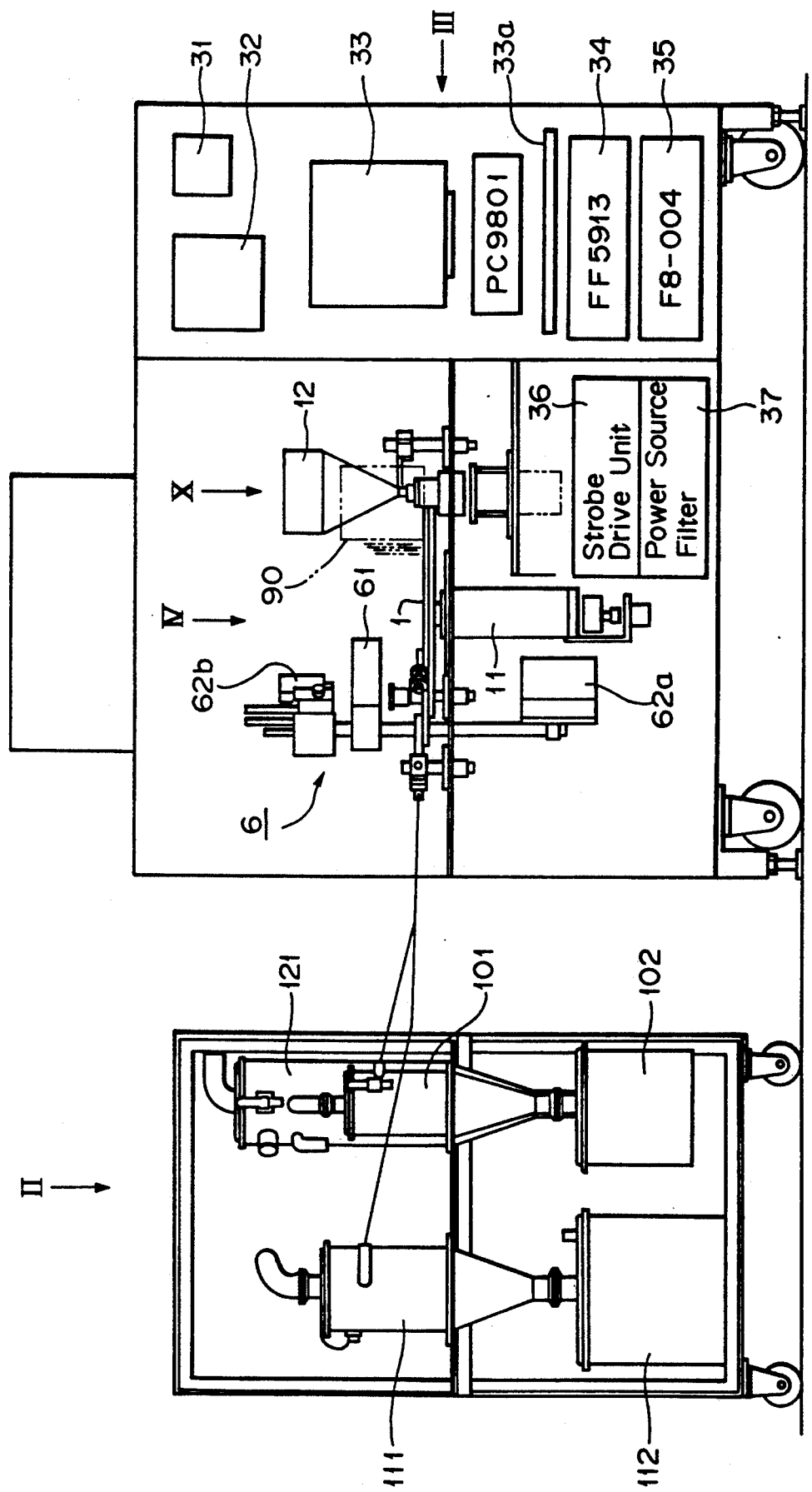
FIG. 1 is a partial cross sectional side view that shows an embodiment of the powder material inspection apparatus according to the present invention.
Figure 2:
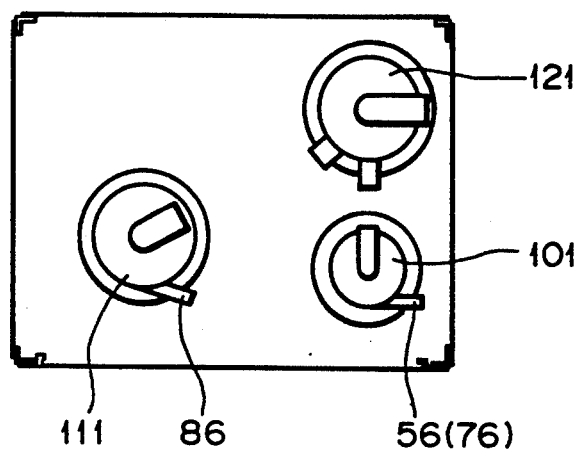
FIG. 2 is a view showing a part of FIG. 1 seen from a direction shown by an arrow II.
Figure 3:
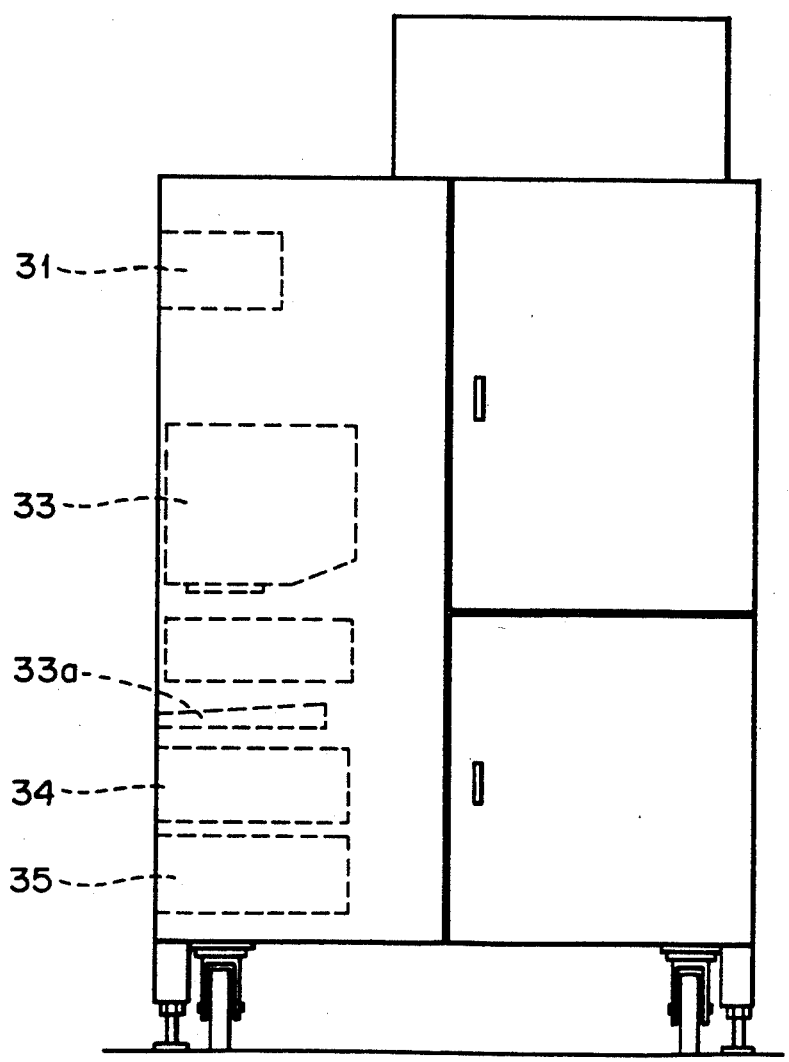
FIG. 3 is a view showing a part of FIG. 1 seen from a direction indicated by an arrow III.
Figure 4:
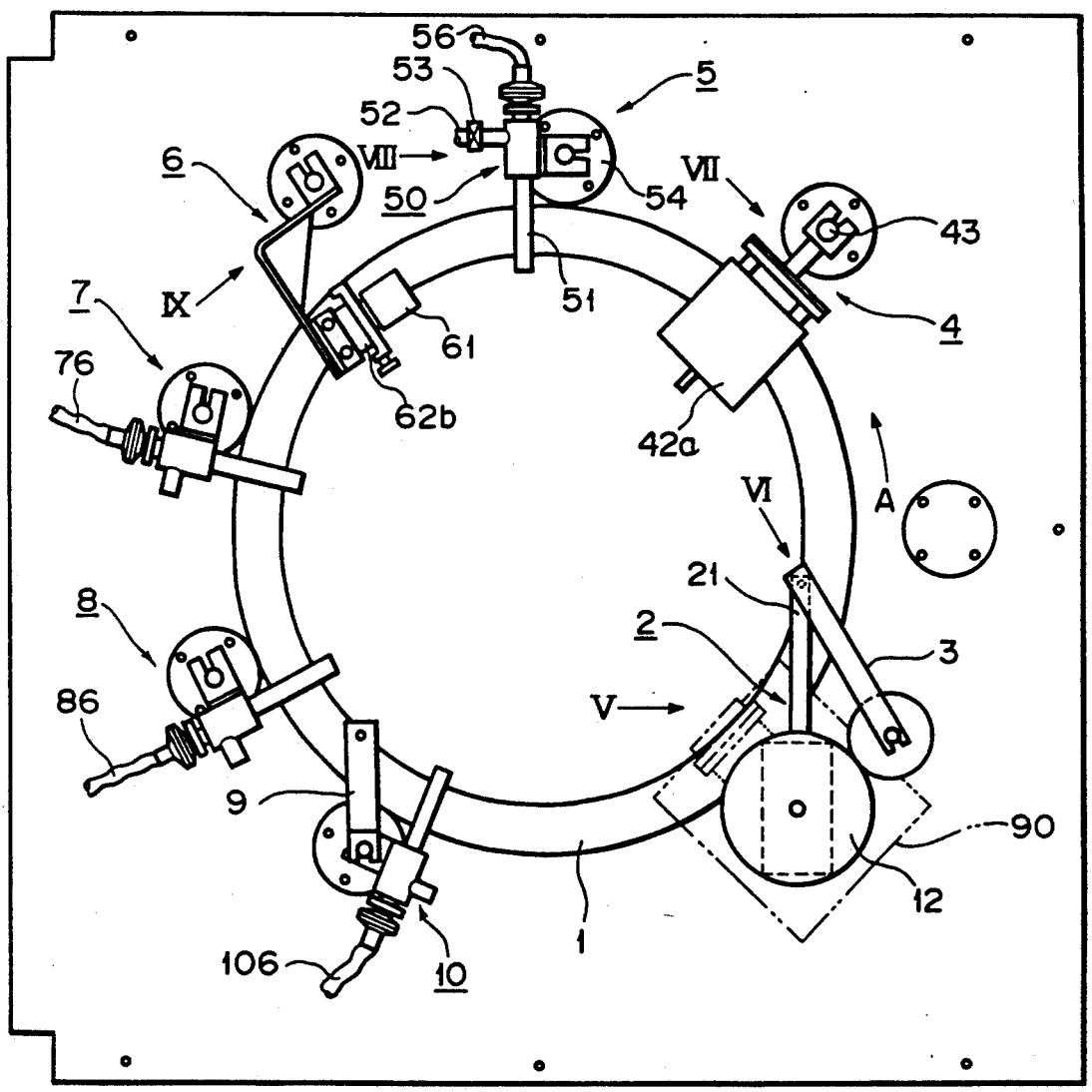
FIG. 4 is a view showing a part of FIG. 1 seen from a direction indicated by an arrow IV.

An embodiment of the present invention will be explained hereunder in reference with the drawings. FIG. 1 is a partial cross sectional side view that shows an embodiment of the powder material inspection apparatus according to the present invention, FIG. 2 is a view showing a part of FIG. 1 seen from a direction shown by an arrow II, FIG. 3 is a view showing a part of FIG. 1 seen from a direction indicated by an arrow III, and FIG. 4 is a view showing a part of seen from a direction indicated by an arrow IV; As shown on FIG. 4, near the periphery of a rotary table 1, there are consecutively installed, a feeder 2 which supplies an object to be inspected such as powder material onto the upper surface of the rotary table 1 in a manner that the powder material is lined up in a single layer thereon, a first static electricity remover 3 which removes the static electricity from the powder material, a first foreign material inspector 4 that photosenses and detects the foreign material contained in the powder material from the under surface side of the rotary table 1, a first foreign material remover 5 that sucks and rejects the foreign material contained in the powder material as detected by the first foreign material inspector 4, a second foreign material inspector 6 that detects the foreign material contained in the powder material by photosensing the same from the upper surface side of rotary table 1, a second foreign material remover 7 that sucks and rejects the foreign material contained in the powder material detected by the second foreign material inspector 6, a good product remover 8 that sucks and removes the powder material from which the foreign materials are removed, a second static electricity remover 9 that removes the static electricity from the slightly remaining powder material on the surface of the rotary table 1, and a cleaner 10 that sucks and removes the slightly remaining powder material on the surface of rotary table 1.

Rotary table 1 is formed of, for example, a colourless transparent glass plate and is disc-shaped with a flat surface. Under the rotary table 1, a rotation drive mechanism 11 is installed as shown on FIG. 1. The rotation drive mechanism 11 is equipped with a rotor shaft that is coupled to the center of rotary table 1 that is horizontally installed and a motor which rotates the rotary shaft at a predetermined speed (both not shown in the drawings).

Figure 5:
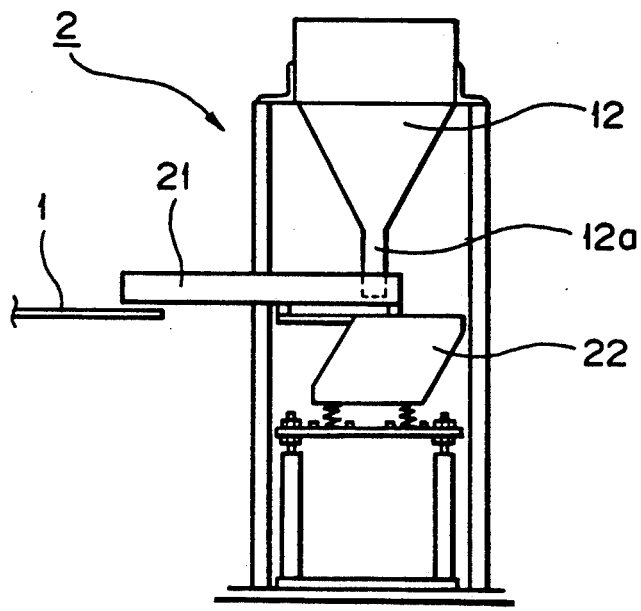
FIG. 5 is a view showing a part of FIG. 4 seen from a direction of an arrow V.
Figure 6:
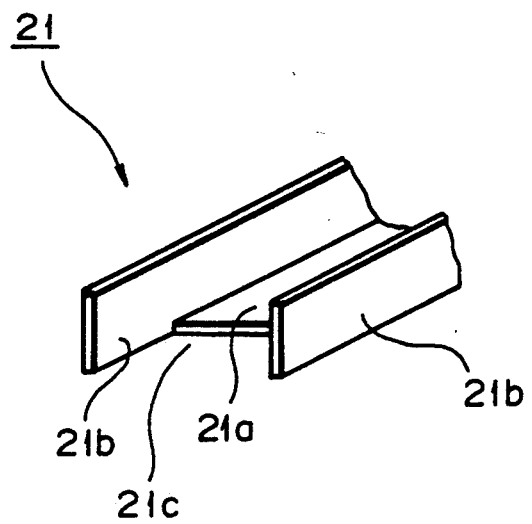
FIG. 6 is a view showing a part of FIG. 4 seen from a direction of an arrow VI.

FIG. 5 is a view showing a part of FIG. 4 seen in a direction indicated by an arrow V and shows the feeder 2. In FIG. 5, 21 is a trough and the trough 21 is a gutter with a U-shaped cross section as shown on FIG. 6 which shows a part of FIG. 4 seen in a direction indicated by an arrow VI. This trough 21 is constructed by a bottom plate 21a and both side walls 21b in the length direction thereof. Above and under one end of trough 21, there are located a hopper 12 and an electro-magnetic coil 22 that applies vibration to the trough 21 in a manner that a bottom side outlet 12a of the hopper 12 is located inside one end portion of the trough 21. The other end of the trough 21 is located above the rotary table 1. Further, at a tip end of bottom plate 21a a cutout 21c is formed so that both side walls 21b are longer than the bottom plate 21a by that much. Also, the vibration provided to trough 21 by the electro-magnetic coil 22 is arranged so that the powder material that is transferred to the tip end of bottom plate 21a is positively arranged in a single layer.

Figure 7:
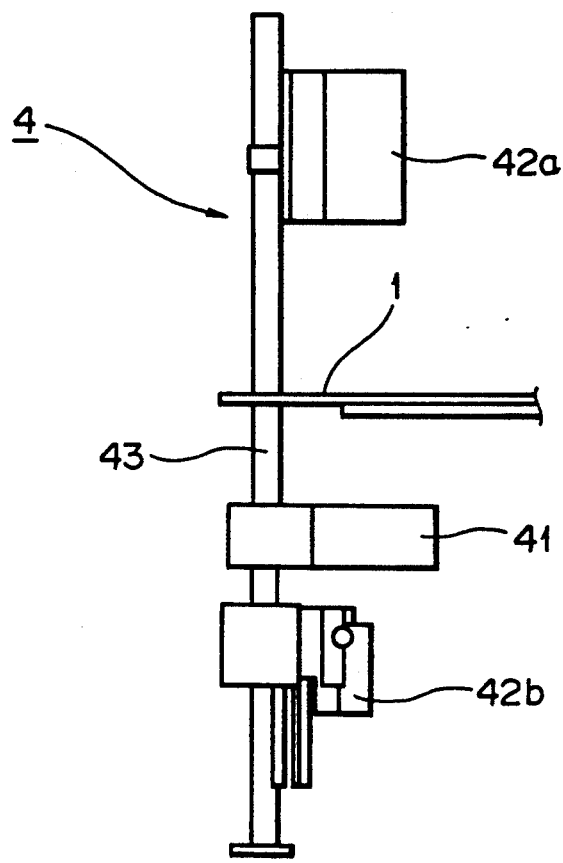
FIG. 7 is a view illustrating a part of FIG. 4 seen from a direction of an arrow VII.

FIG. 7 is a view showing a part of FIG. 4 seen in the direction indicated by an arrow VII and shows the first foreign material inspector 4. This foreign material inspector 4 is equipped with a television camera 41 and two strobes 42a, 42b. Strobe 42a is located above the rotary table 1, whereas strobe 42b is located with the television camera 41 under the rotary table 1 in opposing position to strobe 42a. 43 is a support stand that supports the television camera 41, strobe 42a, strobe 42b, moveable in the up and down direction.

Figure 8:
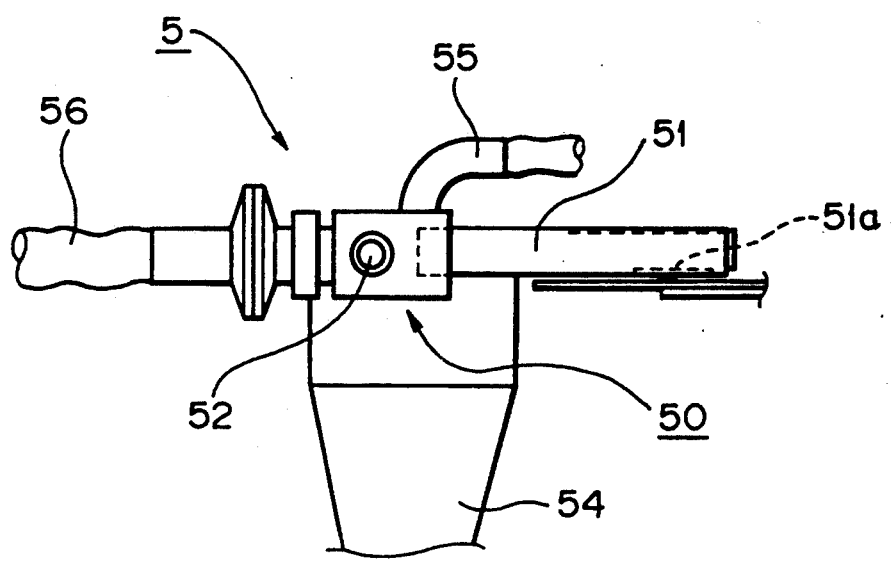
FIG. 8 is a view showing a part of FIG. 4 seen from a direction of an arrow VIII.

FIG. 8 shows a part of FIG. 4 seen in the direction indicated by an arrow VIII that illustrates the first foreign material remover 5. In FIG. 8, 50 is a suction ejector which consists of suction pipe 51, air inlet pipe 52 and valve 53 (FIG. 4). A suction nozzle 51a at the tip end of suction pipe 51 is located close to the surface of the rotary table 1 so that the suction nozzle 51a will positively absorb the foreign material on the surface of rotary table 1 and also the plane of the suction nozzle 51a is in parallel with surface of the rotary table 1. Also, the other end of the suction pipe 51 is communicated to one end of connection hose 56. One end of the air inlet tube 52 is connected to an air compressor (not shown in drawings) while the other end thereof is connected to the suction pipe 51 so that it will blow air in the opposite direction to the suction nozzle 51a. Valve 53 serves to adjust the air flow within the air inlet tube 52. 55 is an air blow-out hose that is connected with the upper part of cyclone 54, where this hose 55 is connected to the dust collector (not shown in drawings). Further, the second foreign material remover 7, good product remover 8 and cleaner 10 are of the same structure to the first foreign material remover 5.

The connection hose 56 of the first foreign material remover 5 and a connection hose 57 of the second foreign material remover 7 are both connected to a foreign material cyclone 101 (FIG. 1) so that the foreign materials that were absorbed by the foreign material removers 5, 7 are separated from the air in cyclone 101 and then collected in a collection box 102 (FIG. 1). At the same time, the absorbed powder material by the good product remover 8 is sent to a good product cyclone 111 (FIG. 1) through a connection hose 86, and is separated from the air therein and then collected in collector 112 (FIG. 1), while the powder material or the like that is absorbed by the cleaner 10 is sent through a connection hose 106 to a cyclone filter 121 (FIG. 2) where it is collected.

The first foreign material remover 5 is installed in genged relation to the first foreign material inspector 4 as well as the rotation drive mechanism 11 so that suction nozzle 51a absorbs the foreign materials that were detected by the first foreign material inspector 4 and arrived a the place beneath the suction nozzle 51a of the suction ejector 50. Also, the second foreign material remover 7 is set up in the same manner against the second foreign material inspector 6.

Figure 9:
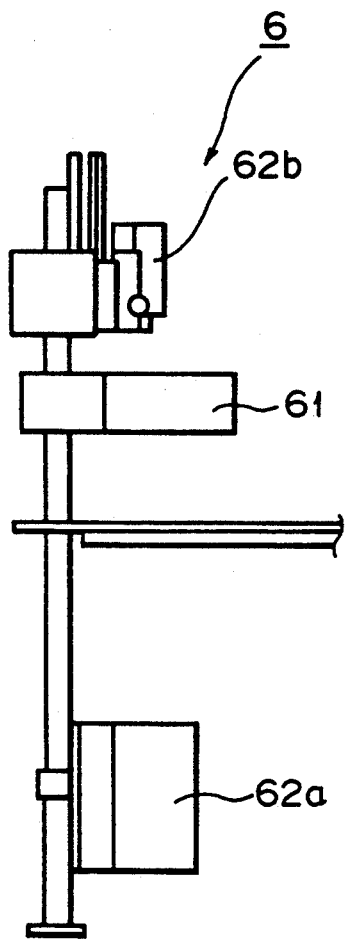
FIG. 9 is a view showing a part of FIG. 4 seen from a direction of an arrow IX.

FIG. 9 shows a part of FIG. 4 seen in the direction indicated by an arrow IX that illustrates the second foreign material inspector 6. This inspector 6 comprises television camera 61, strobe 62a, 62b, whereas the upper and lower relation against the rotary table 1 thereof is the reverse to that of the first foreign material inspector 4. In other words, the television camera 61 and strobe 62b are located above the rotary table 1 while the strobe 62a is installed under the same.

Further, on FIG. 1, 31 is a printer that prints out the inspection data, 32 is a monitor that displays the images from television cameras 41 and 61, 33 is a computer that controls the operation of the entire apparatus and also memorizes the inspection data, 33a is a keyboard for the same, 34 is an image signal processor, and 35 is an image analyzer, where these make judgements whether or not foreign materials are contained in the powder material by analysing the image signals from the television cameras 41, 61. 36 is a strobe drive unit that controls the frequency etc. of strobes 42a, 42b, 62a, 62b, and 37 is an power source filter that adjusts the power source.

In this case, when the image signal processor 34 and the image analyzer 35, which receives the output signal from the television camera 41 (or 61), detect that a foreign material exists in the powder material in the visual field of the television camera 41 (or 61), the detected signal is supplied to the computer 33 which then stores the detected data and supplies the drive signal to the first (or second) foreign material remover 5 (or 7) to drive the same in such a timing that the foreign material thus detected arrives at the position beneath the foreign material remover 5 (or 7) by the rotation of the rotary table 1 so that the foreign material is removed from the rotary table 1 by the absorption ejector 50 of the foreign material remover 5 (or 7).

Further, the first and second foreign material removers 5, 7, the good product remover 8 and the cleaner 10 are same in structure but it may be possible that, for example, the removing or absorbing powers thereof are made different dependent upon their purpose to remove only the foreign material or all the good product o the rotary table 1.

Further, the first and second static electricity removers 3, 9 and the cleaner 10 are always driven illrespective of the existence or absence of the foreign material.

As the next step, the operation of the above-mentioned apparatus will be explained. The powder material to be inspected, that is picked from the production line and accumlated in hopper 12, is cutout in a constant amount each time by trough 21 which is vibrated by the electromagnetic coil 22, and falls through the cut-out 21c as shown on FIG. 6 to be placed on the surface of the rotary table 1 in a condition that is lined up in one direction. Also, at the time the powder material is line up, the static electricity of the powder material is removed by the first static electricity remover 3 (FIG. 1).

The powder material that is lined up on the surface of the rotary table 1 is conveyed by the rotary table 1 which is rotated at a predetermined speed in the arrow direction A (FIG. 4) by the rotation drive mechanism 11 (FIG. 1), so that it first passes over television camera 41 of the first foreign material inspector 4 (FIG. 7) to be photosensed from the underside thereof. At this time, the powder material is photosensed as it is intermittently irradiated by strobes 42a, 42b so that the foreign material contained in the powder material is detected. At that time, since the glass plate that forms the rotary table 1 is transparent, strobe 42b will also irradiate the powder material on the surface of rotary table 1 from its back side. That is to say that the powder material shall be irradiated from both of the front and back sides of the rotary table 1 so that there will be no shadow occurence of the powder material on the surface of the rotary table 1 by the strobe irradiations, and hence such shadow cannot cause a mistaken detection.

Then, the foreign material contained in the powder material is absorbed by the suction nozzle 51a of the first foreign material remover 5 (FIG. 4). At this time, the surface of the rotary table 1 being hard, the suction nozzle 51a shall not be choked by the surface of the rotary table 1 which is flexed by the suction power of the suction ejector 50.

Further, since the surface of rotary table 1 is flat and the suction nozzle 51a is installed to be in parallel to the surface of rotary table 1, the suction power from ejector 50 will affect the surface of rotary table 1 evenly. Therefore, the entire volume of the powder material that is beneath the suction nozzle 51a is entirely effected by the absorption power. The absorbed foreign material passes through connection hose 56 to be blown into cyclone 101, and is separated with air upon circulating inside cyclone 101. The separated foreign material is accumulated inside collector 102.

The powder material that passes under the first foreign material remover 5, then passes under the television camera 61 of the second foreign material inspector 6 where it is photosensed from above this time so that the foreign material contained in the powder material is detected.

Thus, the detected foreign material is absorbed and removed when it passes under the second foreign material remover 7. The absorbed and removed foreign material passes through the connection hose 76 and is sent to cyclone 101, separated with air and accumulated in collector 102.

Then, the powder material which has had the foreign materials removed or which is the good product, is suction removed from the surface of rotary table 1 by the good product remover 8, passes through the connection tube 86 to be sent to cyclone 111 and is separated with air and accumulated in collector 112.

The powder material that was not removed in spite of passing under the good product remover 8, after static electricity removal by the second static electricity remover 9, is absorbed and removed form the surface of rotary table 1 by the cleaner 10.

According to such above described embodiment of powder material inspection apparatus of the present invention, the powder material that is loaded on the surface of rotary table 1 and conveyed is arranged so that the foreign material contained in the powder material is detected by photosensing from both of the front and back side of the rotary table 1 by television cameras 41, 61 so that such foreign material that may possibly be overlooked by inspection from only one side of the front or back of the rotary table 1, can be positively detected which raises the reliability of the powder material good products.

Further, since the rotary table 1 is hard and its surface is flat, the rotary table 1 shall not be flexed or deformed by the suction of foreign material removers 5, 7, good product remover 8 and cleaner 10. Therefore, it is possible to place the suction nozzles of the suction ejectors close to the surface of rotary table 1 so that the powder material will be positively absorbed by the suction ejectors while at the same time make remover 5, 7, 8 and cleaner 10 absorption power function evenly to the surface of rotary table 1. Therefore, the powder materials or the like on the surface of rotary table 1 are practically completely removed. Accordingly, the foreign materials can be completely removed and the good product reliability can be raised.

Also, the residual powder material on the rotary table 1 can be practically removed entirely by cleaner 10, so that the mixture of the powder material after inspection with the powder material prior to inspection can be prevented.

Moreover, since the rotary table 1 is transparent and at the inspection by the foreign material inspector 4 (or 6), the two strobes 42a, 42b (or 62a, 62b) are arranged to irradiate the powder material on the surface of rotary table 1 from its both front and back sides, the shadow occurence of the powder material on the surface of rotary table 1 by the strobe irradiations is prevented and therefore the erroneous detection of such shadow as a foreign material can be prevented so that the foreign material inspection reliability is further raised.

Further, on the surface of rotary table 1, the powder material is arranged so as not to be piled up and to be in a lined up single layer condition upon loading by the trough 21, so that the overlooks of the foreign material being hidden at the inspection by the foreign material inspector can be prevented. Therefore, the inspection reliability can be further raised.

Furthermore, since the foreign material contained in the powder material is accumulated in the collector 102 (FIG. 1), a further detailed inspection on the characteristics of the foreign material can be made.

Figure 10:
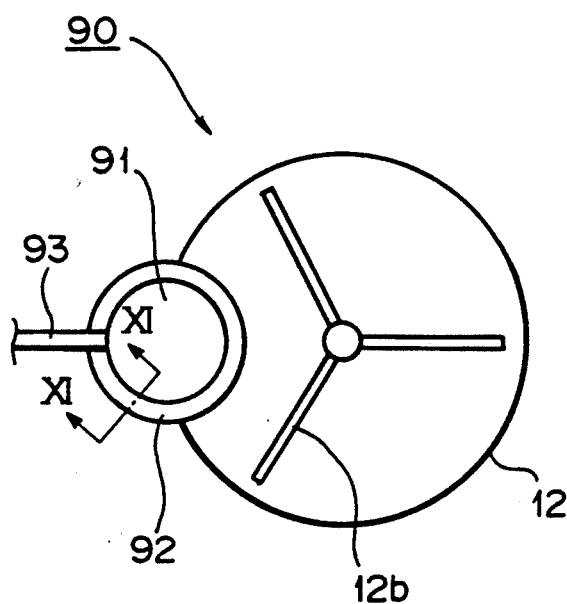
FIG. 10 is a cross sectional view showing a part of FIG. 1 seen from a direction of an arrow X.

As another embodiment of the present invention, instead the feeder 2 that has trough 21, a table feeder 90 as shown on FIG. 10 may be used.

Figure 11:
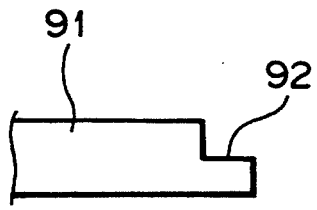
FIG. 11 is a cross sectional view along a line XI—XI in FIG. 10.

Such table feeder 90 is shown on FIG. 1 and FIG. 4 by a two-dot chain line. FIG. 10 shows a part of FIG. 1 seen in the direction indicated by an arrow X. Also, FIG. 11 is a cross section diagram on the line XI—XI in FIG. 10.

This table feeder 90 carries and conveys the powder material from hopper 12 in a groove 92 formed along the outer periphery of a rotating disc type feeder 91, whereas a scraper 93 drops the powder material in groove 92 onto the surface of rotary table 1. Further, in the bottom part of hopper 12, there is a rotary blade 12b installed which serves to evenly move down the powder material inside the hopper 12.

Further, the foreign material removers 5, 7, good product remover 8, and cleaner 10 may partially or totally be structured to not necessary only suction removal, but also may be of a blow off removal type.

Also, the first and second static electricity removers 3, 9 may be one or both omitted.

It will be apparent that many modifications and variations could be effected by one skilled in the art without departing from the spirits or the scope of the novel concepts of the present invention so that the spirits or scope of the present invention should be determined by the appended claims only.

I claim as my invention:

1. Apparatus for automatically detecting and removing foreign matter from powder material comprising a disc-shaped transparent rotary table for conveying powder material on its surface, said rotary table having a circumferential groove on its upper surface adjacent the periphery thereof, a feeder for supplying a stream of powder material to said groove in a single uniform layer, a photosensing system scanning said powder material on said rotary table from above and below said rotary table to detect the presence of foreign matter in said powder material, means for removing the detected foreign matter from said groove and means for thereafter removing the powder material remaining in said groove after the foreign matter has been removed.

2. The apparatus according to claim 1, wherein said transparent rotary table comprises a glass plate.

3. The apparatus according to claim 1, wherein said feeder comprises a hopper for dispensing powder material, a trough having one end located at said hopper to receive said dispensed powder material and one end located above said rotary table, means for vibrating said trough to disperse said powder material and to deposit said dispersed powder material onto said rotary table in a single layer.

4. The apparatus according to claim 1, wherein said photosensing system comprises a television camera and stroboscopic illuminating means located above and below said rotary table.

5. The apparatus according to claim 1, wherein each of said foreign matter removers and said powder material removers are absorption ejectors.

6. The apparatus according to claim 1, including means for removing static electricity from said powder material prior to said powder material being subject to said photosensing system.

7. A power material inspection apparatus according to claim 1, further comprising a printer for printing out detected data, a monitor for displaying thereon a video image from said photosensing system, a computer for controlling the complete operation of said inspection apparatus and for storing the detected data, a processor for processing a video signal from said photosensing system, an image analyzer for analyzing the video signal from said photosensing system to judge whether or not said foreign material exists in said powder material, and a strobe controller for controlling lightening timing of said strobes.

8. A powder material inspection apparatus according to claim 7, further comprising a cyclone which is in communication with the foreign material remover for separating the foreign material from air and a collector for collecting said foreign material from said cyclone.

9. A powder material inspection apparatus according to claim 8, further comprising a good product cyclone which is in communicatiokn with the powder material remover for separating the powder material without foreign material present therein from air and a collector for collecting said powder material from said good product cyclone.

* * * * *